April 15, 1952 K. E. WILLIAMS ET AL Plant Pat. 1,082
IVY PLANT
Filed Aug. 18, 1950
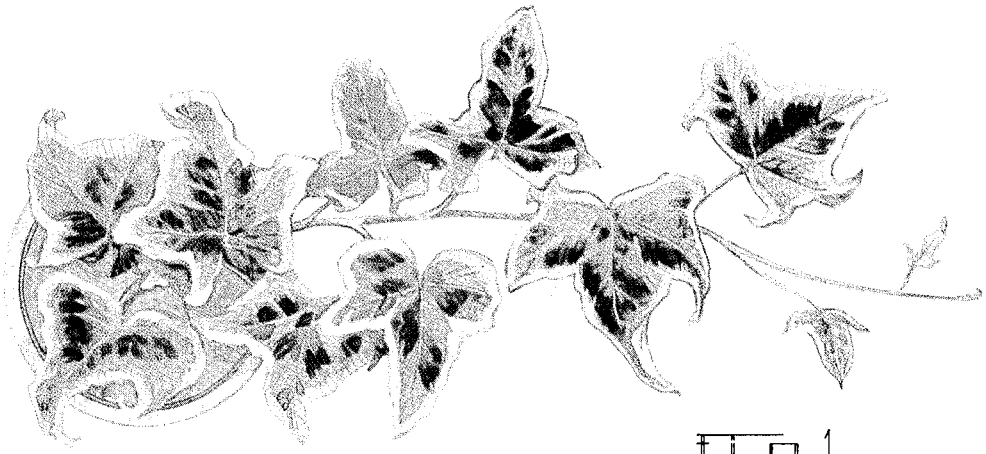
Fig. 1
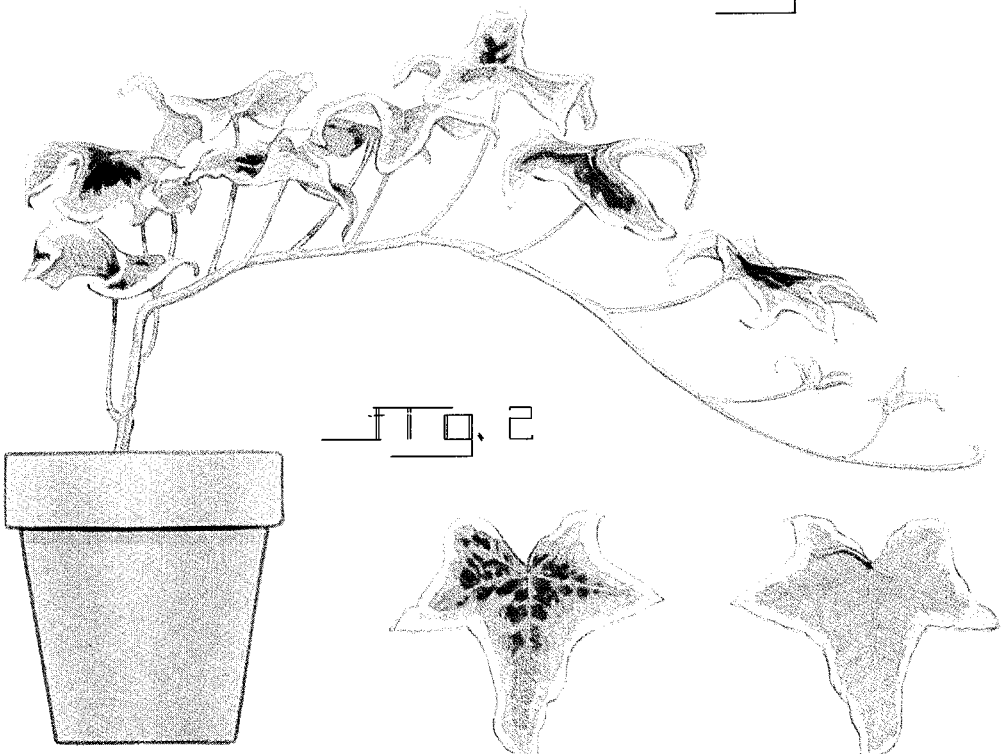
Fig. 2
Fig. 3
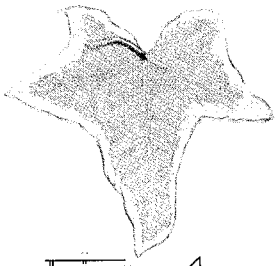
Fig. 4
INVENTORS
KEITH E. WILLIAMS
ESTHER M. WILLIAMS
BY Toulmin & Toulmin
ATTORNEYS Patented Apr. 15, 1952

Plant Pat. 1,082

UNITED STATES PATENT OFFICE 1,082

IVY PLANT

Keith E. Williams and Esther M. Williams,
Springfield, Ohio

Application August 18, 1950, Serial No. 180,138

1 Claim. (Cl. 47—59)

Our new discovery relates to improvements in ivy, and especially to a new, original and distinct variety of English ivy allied to the genera *Hedera helix* Hibernica of the group "Romosa Complex" originating as a sport of a Glazier variety.

The new Glazier variety originated and has been produced by us by cuttings in our own greenhouses at Springfield, Ohio, the characteristic features appearing to be permanent.

We have asexually reproduced this variety in approximately fifteen hundred (1500) specimens and its distinct characteristics have proved to be firmly fixed.

The new variety has no reproductive organs and does not produce fruit or flowers.

The outstanding characteristics of our new ivy are the shape of the leaves and their multicolor. The color of the leaves comprises a substantially white border, a light green leaf configuration occupying the center of the leaf and a superimposed green portion forming a second leaf design.

The proposed illustrations accompanying these specifications show the following:

Figure 1 is a color rendition of a top plan view.

Figure 2 is a side elevation in colors.

Figure 3 is a color rendition of a typical leaf on the upper side.

Figure 4 is a color rendition of a typical leaf on the under side.

Reference to color plates is based on A Color Notation by A. H. Munsel 10th Ed. 1947.

Where no reference is given, the ordinary dictionary term is intended.

The following is a detailed description of this new variety.

The growth habit is similar to that of other ivies except that it appears to be a very vigorous and rapid growth. The duplication of its color scheme and leaf structure is uniform and repetitive.

The most outstanding characteristics are the multicolor leaf and the leaf form.

The stem is dark green. The leaf petioles are mounted upon the stem on opposite sides alternately. The inner nodes are generally substantially uniform.

The leaf is deep cut and the tips of the leaves are curled downwardly in a sharp arc while the edges of the leaves are wavy or undulated.

The leaf formation as to its color is one provided with a substantially ivory white border (Munsel group 8) with a greenish tinge and within this border the outline background is light apple green (Munsel group 11) of a similar leaf structure. Superimposed upon this light green is another substantially complete leaf structure of dark emerald green (Munsel group 12). The surfaces of the white border and of the dark green have a higher degree of light reflectivity than the light green intermediate portion of the leaf.

Having thus disclosed by discovery, we claim:

A new and distinct variety of ivy plant, substantially as shown and described, characterized particularly by a five pointed leaf with fluted, undulated edges, deep cut, with the points relatively sharp and the color comprising a greenish ivory white border, the light green leaf design substantially uniformly spaced with the inner edge of said border and occupying the center of the leaf and a dark green leaf design superimposed on the light green area, the dark green design and the greenish white border portions having a higher degree of reflectivity than the light green leaf design, said leaves being arranged on a single stem at intervals alternately on opposite sides of the stem.

KEITH E. WILLIAMS.
ESTHER M. WILLIAMS.

No references cited.